United States Patent [19]

Krieger, Jr.

[11] 4,010,641
[45] Mar. 8, 1977

[54] APPARATUS FOR MEASURING THE STIFFNESS CHARACTERISTIC OF STRUCTURAL ADHESIVES

[75] Inventor: Raymond Buchheimer Krieger, Jr., Abingdon, Md.

[73] Assignee: American Cyanamid Company, Stamford, Conn.

[22] Filed: Oct. 16, 1975

[21] Appl. No.: 623,141

[52] U.S. Cl. .......................... 73/150 A; 33/147 D; 336/30
[51] Int. Cl.² ................. G01N 19/04; G01B 7/24
[58] Field of Search ............... 73/150 R, 150 A; 33/147 D, 148 D; 336/30

[56] References Cited
UNITED STATES PATENTS

| | | |
|---|---|---|
| 2,119,076 | 5/1938 | Dietrich ............... 33/148 D X |
| 2,293,289 | 8/1942 | Gadd ..................... 33/148 D |
| 2,543,429 | 2/1951 | Wood ................. 33/148 D X |
| 2,767,476 | 10/1956 | Strimel ................. 33/148 D |
| 3,577,775 | 5/1971 | Henderson ........... 73/150 A X |
| 3,608,365 | 9/1971 | Baucom et al. ....... 33/147 D X |

*Primary Examiner*—Herbert Goldstein
*Assistant Examiner*—John S. Appleman
*Attorney, Agent, or Firm*—Frank M. Van Riet

[57] ABSTRACT

An apparatus for measuring the stiffness characteristic of structural adhesives which encompasses a critically patterned series of sensor points which functions cooperatively with a novel mounting mechanism to enable the recording of minute movements of a bonded specimen to which force is applied with exacting precision.

9 Claims, 9 Drawing Figures

APPARATUS FOR MEASURING THE STIFFNESS CHARACTERISTIC OF STRUCTURAL ADHESIVES

BACKGROUND OF THE INVENTION

The use of adhesives to bond materials to one another is becoming more and more wide-spread and, as a result, it is becoming more and more necessary to learn as much about each individual adhesive system in question when considering which to use for a particular service application. Skilled artisans are constantly searching for new and useful techniques which will enable them to chose one adhesive over another when confronted with a multitude of systems, each of which will apparently do the job.

One of the fields of exploration which has recently become of more concern to the artisan is in the area of stress analysis. The artisan must be able to predict the strength and durability of a particular adhesive system when considering its use. These features of adhesive systems have been very difficult to assess with any degree of particularity because commercially available devices which are designed to accumulate data of this sort have not proven accurate enough, not only from the standpoint of giving false or misleading information but from the standpoint of not being capable of detecting the minute movements involved when test samples are subjected to extraneous forces. Devices now in general use are subject to so many influencing factors that readings obtained therefrom are, in most instances, meaningless. Some of these influencing factors include (1) loading holes off center in producing specimen, (2) glue line voids off center in producing specimen, (3) glue line rotation during exertion of force on specimen, (4) adherend bending rotations of material when force exerted on specimen, (5) adherend tension differential of material during applications of force on specimen (6) adherend shear deformation as force is exerted on specimen and the like. Each of these individual occurences are normally manifested during specimen tests and, consequently, each adds its influence to the final information received during the testing program. Other errors are introduced into the calculations by deficiencies inherent in the design of the testing apparatus, e.g., lever systems tend to include "slop" or play in the bearings or pivotal points thereof because lever ends move on arcs rather than in straight lines.

A complete and precise discussion of evaluation techniques and stress analysis for structural bonds under hostile environment can be found in an article in Adhasion, Vol. 18, No. 12, December 1974, published by Bertelsmann Fachzeitschriften GmbH, and continued in Vol. 19, No. 1, January 1975, said article having been authored by the instant inventor.

SUMMARY

I have now discovered a new and useful apparatus for obtaining stress data of adhesives so as to enable one to predict the strength and durability of that adhesive in a particular application. My new apparatus enables the stress analysis of structurally bonded components such as those useful in aircraft, missiles and space vehicles, so as to predict their strength, by obtaining a property of the adhesive called the shear stiffness, as described in the above articles.

My novel apparatus is not subject to errors produced by false strain signals from extraneous deformation of the test specimen, as discussed above, or from such errors as produced in lever systems which transform specimen strain to transformer core movement using bearings or pivot points which move on arcs rather than on straight lines. The instant apparatus overcomes these false signals because the sensor points that grip the specimen are arranged so that only the shear movement of the glue line can cause relative movement between the sensor points. Because the sensor points are close to the glue line, are on a line through the center of gravity of the instrument and double points are used on one side only, the instrument can rotate with small loads on the sensor points so they do not slip and cause error. Also the double point configuration minimizes error from tension strain. Since an instrument is mounted on each side of the test specimen, errors from eccentric or unsymetrical specimens are eliminated. Furthermore, strain motion is transferred by fixed end beam springs rather than other arc-related means so as to eliminate non-linear motion induced errors.

DESCRIPTION OF THE INVENTION INCLUDING PREFERRED EMBODIMENTS

As mentioned briefly above, the apparatus of the instant invention is used to measure the relative movement or displacement between two adhered materials as represented by the movement of sensor points in the device. The device uses a linear, variable, differential transformer to detect the specimen movement from the sensor points and transmits a signal through an amplifier to a recorder. Calculation, using the recorded information, enables one to obtain the relative shear strength of the adhesive and thereby predict its ultimate strength and durability.

Figure 1:
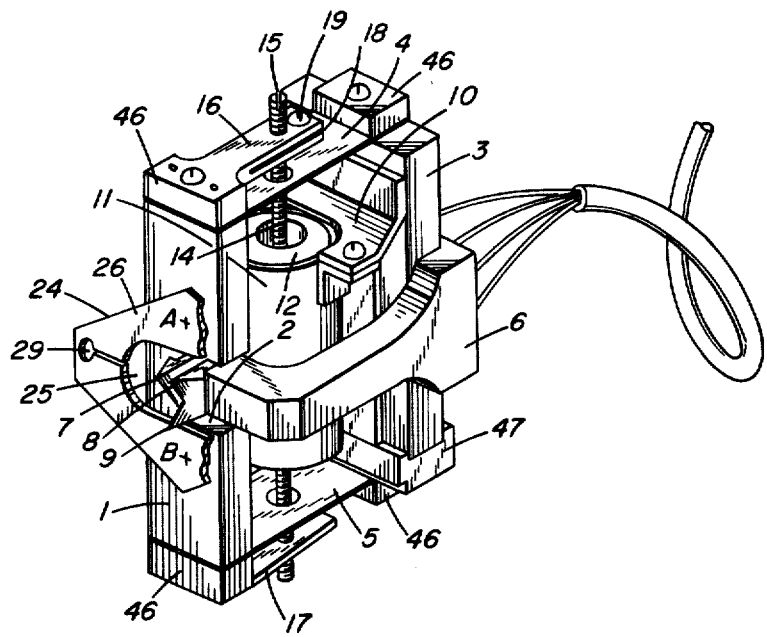
FIG. 1 is an isometric view of the complete extensometer of the instant invention, the frame locking mechanism excluded.
Figure 2:
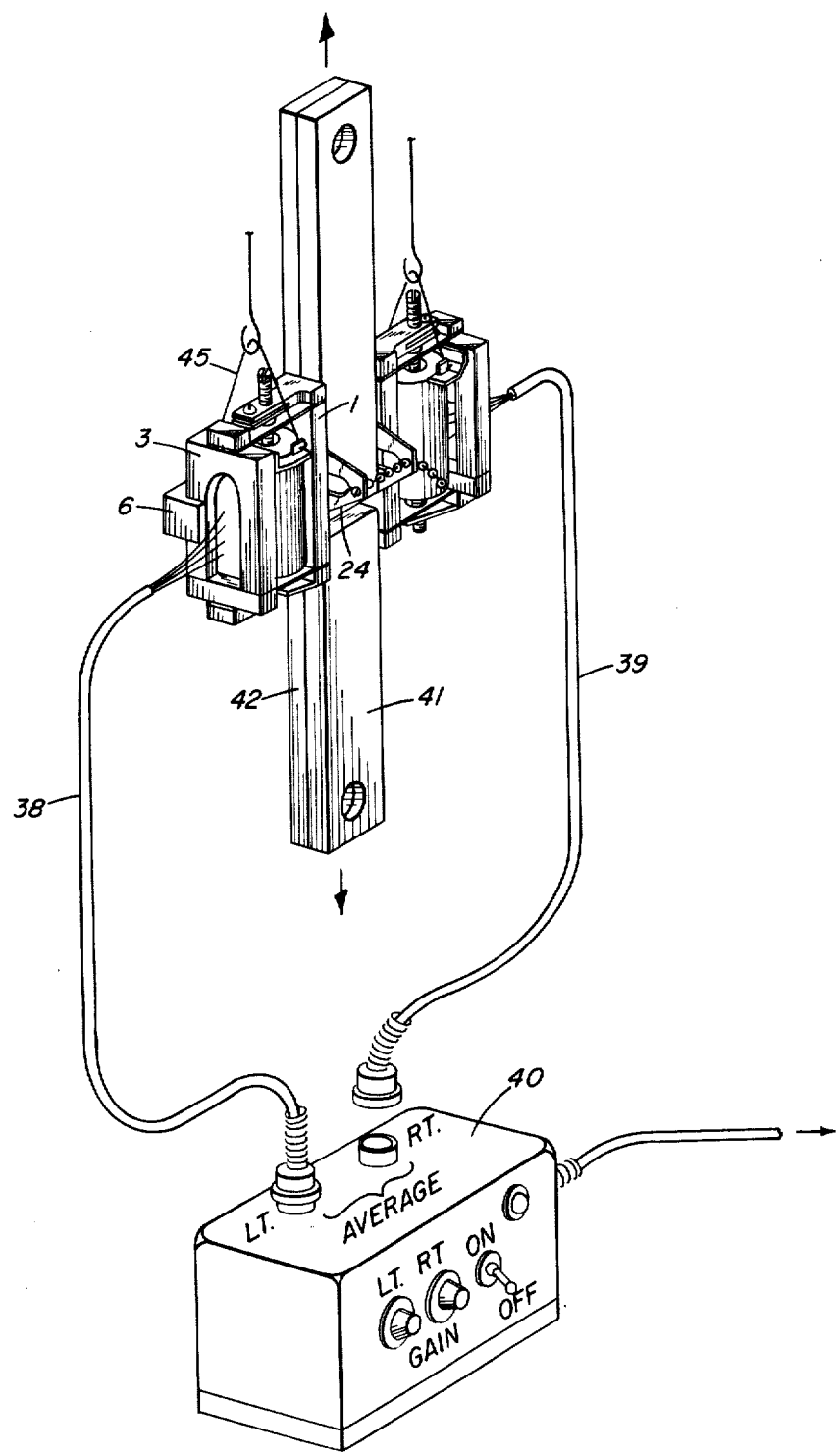
FIG. 2 is an isometric view of a pair of the instant instruments positioned on a bonded specimen preparatory to analysis thereof, showing the electronic hook-up thereof to an amplifier and recorder.
Figure 5:
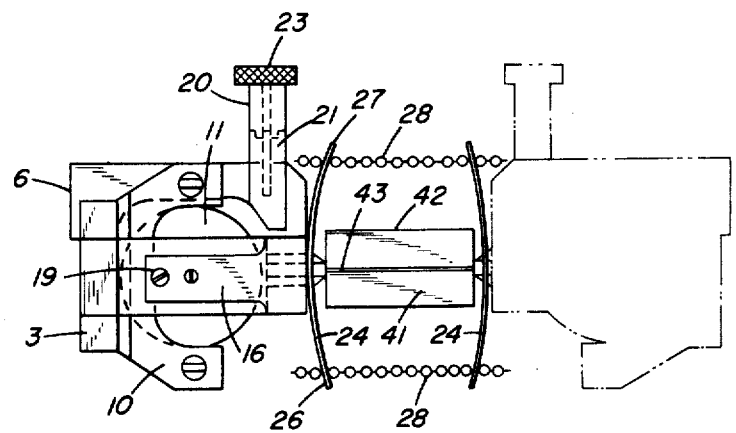
FIG. 5 is a top schematic view showing the mirror-image pair of instruments mounted on a sample with one instrument in phantom.

Referring now to FIG. 1, the complete device, except for the frame locking means best seen in FIG. 5, is shown. The device is comprised of a first frame 1 having an aperture 2 therein, more fully seen in FIG. 3. A second frame 3 constitutes the rear of the apparatus. Frame 3 can be of any desired configuration but should contain a conduit as seen in FIG. 2 for attaching a recording wire to the transformer. Plates 1 and 3 are connected at their upper sections by first plate spring 4 which is fully fixed, and at their lower sections by second plate spring 5 which is also fully fixed. By "fully fixed" is meant that the plate springs are so attached to the frames that no rotation about any of the three possible axes at their points of attachment is possible. The only allowable movement is up and down relative to the frames. Fixity bars 46 accomplish this result.

There is a supporting member 6 on second frame 3 which extends to frame 1 and movably fits into aperture 2. A first sensor point 7 is fixedly mounted on frame 1 within the confines of aperture 2, and second sensor point 8 and third sensor point 9 are fixedly mounted on supporting member or arm 6, also within the confines of aperture 2. The positioning of these sensor points relative to one another and other parts of the device is set forth more fully hereinbelow. The sensor points are immovably mounted onto frame 1 and arm 6 so that they remain in place during the use of the instrument. Sensor points 8 and 9 may be individually mounted to arm 6 but it is preferred that they be constructed such that they are mounted together, i.e., they are preferably cut from the same piece of material. If sensor points 8 and 9 are mounted individually it is extremely important that sensor point 8 does not slip when the apparatus is used. Some slight slippage is tolerable with regard to sensor point 9. The tips of sensor points 7, 8 and 9 must be sharp enough to bite into the material from which the specimen being tested is made.

Figure 3:
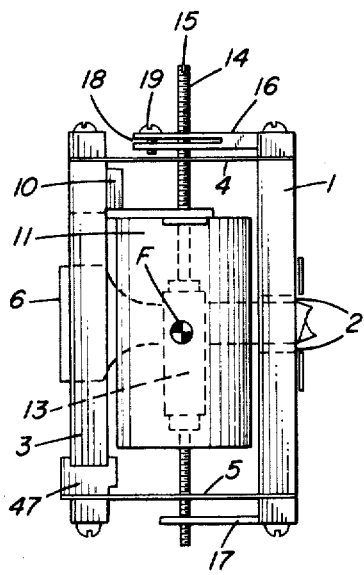
FIG. 3 is a side schematic view of the instrument showing transformer core.

Bracket means 10 is attached to frame 3 and is adapted to support the coil 12 of transformer 11 which is a linear, variable, differential transformer of known configuration comprising coil 12 and a core 13, best seen in FIG. 3. As can be seen, the transformer is positioned within the space formed by frames 1 and 3 and plate springs 4 and 5. Insertion of a new transformer and removal of an old one can be accomplished by removing yoke 47. Adjusting means 14 preferably comprises a threaded rod having a slot 15 at one end thereof which enables the rod to be turned with any suitable device such as a screwdriver. Rod 14 is threadably attached to the top and bottom of frame 1 via ears 16 and 17, respectively. Rod 14 passes through holes in plate springs 4 and 5 but does not touch either component. The core 13 of transformer 11 is attached to adjusting means 14, as seen in FIG. 3, and is positioned within the hollow region of the coil. As can be readily appreciated at this point in this discussion, since the coil of the transformer is attached to frame 3 through bracket 10 and the core of the transformer is attached to frame 1 through rod 14 and ears 16 and 17, the two transformer components are free to move with relation to one another when plate springs 4 and 5 are flexed. It is this configuration which enables the instant device to function.

The adjusting means 14 can be locked in place once the position of the core in the transformer has been adjusted via slot 15, by locking means 18 which comprises a slot in ear 16 and a screw 19. This device prevents accidental rotation of rod 14 once the instrument has been calibrated and mounted on the sample. Locking is effected by tightening screw 19 which causes the slot to be decreased because only the bottom section is threaded, see FIG. 3. It is important that once the core is located within the coil in the necessary position that it be retained at said position throughout the testing routine. The locking system accomplishes this. Techniques other than the slot and screw arrangement described above could be used for this purpose without departing from the scope of the instant invention. Once locked, the core cannot be in contact with the coil and the rod cannot be in contact with the spring plates, as is true also when the locking means is not actuated and the instrument is being prepared for use by adjusting means 14.

Figure 4:
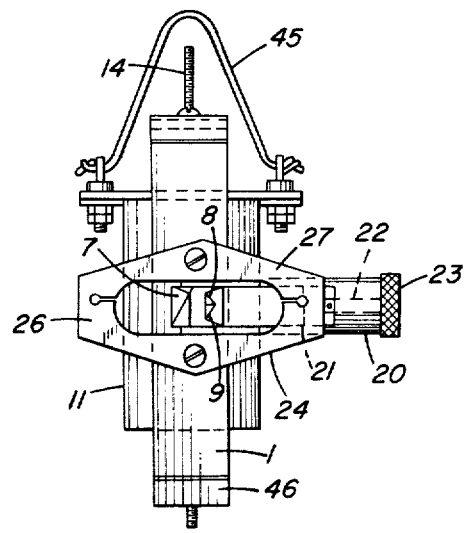
FIG. 4 is a schematic front view of the apparatus showing safety wire and mounting spring-sensor point positioning.

The frames 1 and 3 are also locked in position while the instrument is being stored or while it is being mounted upon the specimen to be tested. Any means can be used whereby the plate springs 4 and 5 are prevented from flexing, either by contacting the spring plates per se or by rigidifying the frames. I have found the latter to be more readily accomplished and therefore preferred. Reference to FIGS. 4 and 5 will best serve to show a useful locking system. Locking means 20 comprises jaw 21 which travels along threaded screw 22 when head 23 is turned and is thrust between arm 6 and frame 1 within aperture 2 thereby rigidifying the entire instrument. Other locking means such as a disc on frame 3 which would fit into a slot on frame 1 could be used.

Figure 8:
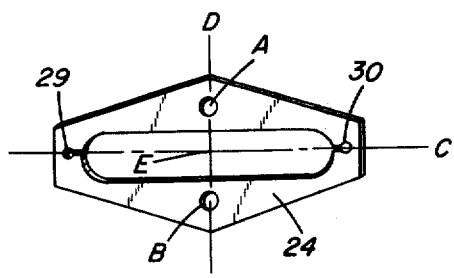
FIG. 8 is a view of the mounting plate spring showing the intersection point made by drawing a first imaginary line through the point of affixation of the spring and a second imaginary line through the attaching means of the spring.

Again referring to FIG. 1, mounting plate spring 24, shown in a sectioned view, has an orifice 25 therein. The orifice is commensurate in size with aperture 2 and is preferably somewhat larger. It is pivotably affixed at its middle to frame 1 at point A. A second pivotal attachment is also preferably positioned at point B. The ends 26 and 27 of mounting plate spring 24, as best seen in FIG. 8, extend beyond the vertical edges of frame 1 and are adapted to receive means for attaching two instruments together. The attaching means 28 can constitute such systems as a ball chain, as is shown, a pair of interlocking hooks, a hook and eye and the like. The mounting plate spring 24 is generally made of a tension or ductile metal such as titanium and serves, along with the attaching means 28, to secure the instrument in position on the specimen being tested.

It is critical that mounting plate spring 24 is attached to frame 1 and not frame 3 in order to prevent plate springs 4 and 5 from buckling when the instrument is being used. As shown in the drawings, the mounting plate spring causes tension on plate springs 4 and 5 which is required. If the mounting plate spring were attached to frame 3, however, engaging attaching means 28 would compress plate springs 4 and 5 and cause them to buckle.

Figure 7:
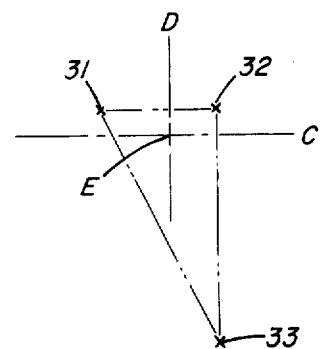
FIG. 7 is a view of the triangle formed by drawing an imaginary line connecting the tips of the sensor points.

As mentioned above, the positioning of mounting plate spring 24 in relation to sensor points 7, 8 and 9 is extremely important. I have found that for proper operation of the instrument, mounting plate spring 24 must be positioned such that the intersection made by a first imaginary line drawn between the points on ends 26 and 27 where attaching means 28 are positioned and a second imaginary line drawn through the point of affixation, i.e., points A and B if two affixation points are used, and parallel to sensor points 8 and 9 and perpendicular to said first imaginary line, falls within the upper portion of the triangle formed by a third imaginary line connecting the tips of three sensor points 7, 8 and 9. That is to say, referring to FIG. 8, imaginary line C drawn through holes 29 and 30 where attaching means 28 is positioned intersects imaginary line D which is drawn through points A and B where the spring is pivotally attached to frame 1, at point E. Point E must be such that it falls within the upper section of the triangle, see FIG. 7, formed by connecting the tips 31, 32 and 33 of sensor points 7, 8 and 9, respectively, with a third imaginary line. If there is only one pivotal attaching point, i.e., point A, the imaginary line therethrough is drawn perpendicular to line C and parallel to the line between points 32 and 33. In this manner, mounting plate spring 24 enables all three sensor points to be held securely against the surface of the specimen to be tested and retains the instrument's position on the specimen, even if one of the points does not touch the specimen while the other two do. The combination of the pivotal attachment and the position of the mounting spring on the frame achieve this effect. The mounting plate spring is therefore pivotal about an axis represented by line D.

Figure 6:
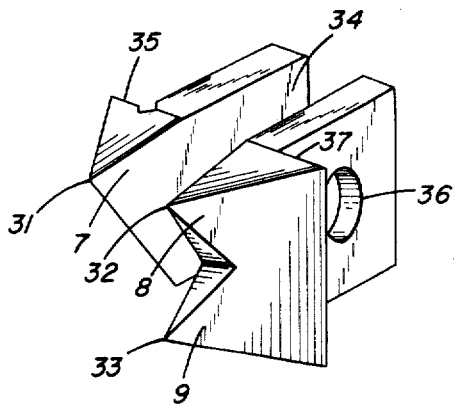
FIG. 6 is an isometric view of the sensor points and their positioning relative to one another.

Sensor points 7, 8 and 9 are also positioned in a manner critical to the operability of the instant apparatus. They are positioned such that sensor points 7 and 8 are in the same horizontal plane with respect to frame 1, sensor points 8 and 9 are in the same vertical plane with respect to frame 1, sensor point 9 is below sensor point 8 and the tips 31, 32 and 33 are all in substantially the same perpendicular plane, i.e., tips 31, 32 and 33 must be touching the same perpendicular plane. Reference to FIG. 6 clarifies the sensor point positioning and also more clearly indicates how the sensor points are attached to frames 1 and 3. Sensor point 7 is affixed to frame 1 through face 34 and abuts the frame at notched shoulder 35. Sensor points 8 and 9, shown produced in one piece, are affixed to frame 3 via arm 6 through tapered hole 36 and abut arm 6 via notched shoulder 37. Sensor points 7 and 8 are preferably on a line through the center of gravity of the apparatus shown at point F, FIG. 3.

Figure 9:
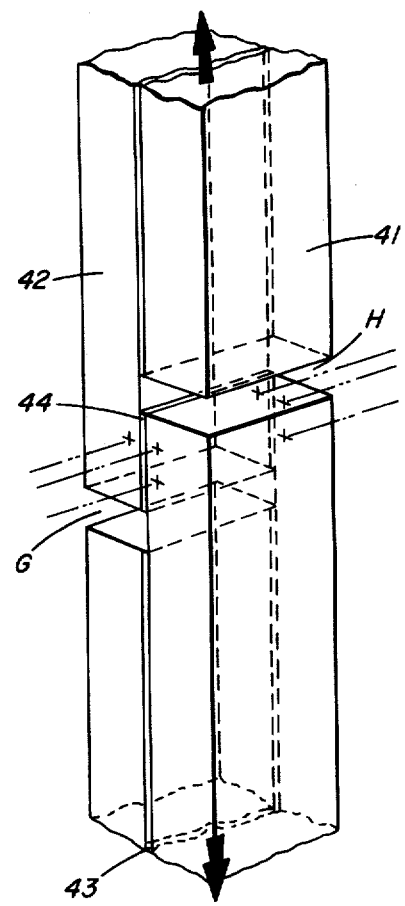
FIG. 9 is an isometric view of a specimen comprising two materials bonded with an adhesive and the positioning thereon of the instrument sensor points.

In operation, the instruments are first adjusted by attaching wires 38 and 39, see FIG. 2, to an amplifier 40 which, in turn, is hooked up to a recorder. Locking means 20 is then engaged so as to lock frames 1 and 3. Screw 19 is loosened to unlock means 18 and the core 13 is adjusted within transformer 11 to its proper position which is determined by a zero voltage signal to the recorder. Means 18 is then set by tightening screw 19 and the instruments are then mounted on the test specimen, see FIG. 2, an enlarged view of which is shown in FIG. 9. As is readily seen, two material sheets 41 and 42 are adhered to one another via glue line 43. The specimen has been cut to the glue line creating slots G and H, leaving a small glue line section 44. The instruments are mounted on the specimen, since they are mirror-images of one another, as shown in FIG. 2 with sensor point 7 away from slot G and biting into sheet 42, and sensor points 8 and 9 biting into sheet 41, as shown as + in FIG. 9. It is preferred that sensor points 7 and 8 be equidistant from the glue line on their respective sheets. Attaching means 28, which are preferably of equal length, are then engaged to their opposite mounting plate springs to thereby suspend the instruments from the specimen. Safety wire 45 can be used, if desired, to prevent damage to the instruments if means 28 fails. The frames are then unlocked and the instruments are ready for use. Although the above description specified that the core adjustment should be accomplished before the instruments are mounted on the test specimen, said adjustment of the core could be carried out after mounting the instruments. However, such is not preferred.

Force is then applied to the test specimen as shown by the arrows in FIGS. 2 and 9. As the force increases, the specimen sheets 41 and 42 begin to move very minutely. Since sensor points 7, 8 and 9 are tenaciously gripping the sheets, they also move. The movement of the sensor points creates a movement in the core of the transformer in relation to the coil and consequently a signal is emitted through wires 38 and 39 and amplifier 40 and are recorded on the recorder.

The instruments are calibrated prior to their use on an actual test specimen by using a dummy specimen composed of a well lubricated plastic sheet sandwiched between two clamped sheets. The instruments are mounted on the dummy specimen as described above and the sheets are then moved a known distance using a calibrated device. The signal again passes to the recorder and, as a result, a record is made of a known deviation in the specimen. Comparison to that recorded movement of the actual specimen results in data which is used to calculate the shear stiffness of the adhesive.

As discussed briefly above, use of the instant apparatus eliminates most of the errors which are common to previously used devices and those which are not eliminated can be compensated for. Specifically, where the specimen is incorrectly fabricated, e.g., the loading holes are off center or the glue line voids are off center, the matching of the signals emitted by both the left and right instruments enables one to either average them out if the difference between them is minor or discard the sample if the difference is gross. Existing devices cannot even detect that the specimen is defective.

When the glue line rotates during the distortion of the specimen, the instant apparatus still emits a valid signal because it is only supported on sensor points 7, 8 and 9 which are at the center of gravity. The rotation does not cause an error as with existing devices which are clamped to the specimen. With regard to adherend bending rotations, since sensor point 7 is opposite sensor point 8, this type of error is minimized so as to be substantially inconsequential.

In the type of error normally produced by adherend tension differential and adherend shear deformation distortions, since stretching of the specimen is tolerated as long as sensor points 7 and 8 are solid and do not move, these errors can be calculated and thereafter subtracted from the first readings obtained. It can therefore be readily appreciated that the six most commonly troublesome errors in adhesion bond analysis have been effectively eliminated by the instant apparatus and that more meaningful data can therefore be obtained therefrom.

I claim:

1. An apparatus adapted to be used in conjunction with a second apparatus having the same structure but of a mirror image configuration for the measurement of the shear stiffness characteristic of structural adhesives so as to enable the accurate stress analysis of an adhesive bond comprising
  A. a first frame having an aperture therein,
  B. A second frame,
  C. A first plate spring fully fixed at one of its ends to the upper section of said first frame and at the other of its ends to the upper section of said second frame, D. a second plate spring fully fixed at one of its ends to the lower section of said first frame and at the other of its ends to the lower section of said second frame, E. a supporting member on said second frame extending movably into said aperture, F. a first sensor point fixedly mounted on said first frame within the confines of said aperture, G. second and third sensor points fixedly mounted on said supporting member within the confines of said aperture, H. bracket means attached to said second frame, I. adjusting means attached to the top and bottom of said first frame, J. a linear, variable, differential transformer comprising a coil and a core, the coil of which is supported by said bracket means and positioned within the space between said first and second plate springs and said first and second frames and the core of which is affixed to said adjusting means and positioned within the hollow of said coil, K. first locking means adjacent said adjusting means and adapted to prevent accidental movement thereof, L. interactive, second locking means positioned adjacent to said first and second frames and adapted, when engaged, to minimize flexing of said first and second plate springs, M. a mounting plate spring having an orifice therein commensurate in size with said aperture, being pivotably affixed at its middle to said first frame, extending beyond the vertical edges of said first frame and having attaching means within the extending portions thereof, said sensor points being positioned such that said first and second points are in the same horizontal plane with respect to said first frame, said second and third sensor points are in the same vertical plane with respect to said first frame, said third sensor point is below said second sensor point and the tips of all three sensor points touch substantially the same perpendicular plane and said mounting plate spring being positioned such that the intersection made by a first imaginary line drawn between said attaching means and a second imaginary line drawn through the point of affixation thereof parallel to said second and third sensor points and perpendicular to said first imaginary line falls within the upper portion of the triangle formed by a third imaginary line connecting said three sensor tips and pivotal only about an axis represented by said second imaginary line.

2. An apparatus according to claim 1 wherein said adjusting means comprises a threaded rod.

3. An apparatus according to claim 1 wherein an ear is affixed to both the top and bottom of said first frame and said adjusting means is threadably engaged therewith.

4. An apparatus according to claim 1 including electrically conductive wire attached to said transformer and adapted to connect to an amplifier.

5. An apparatus according to claim 4 wherein said wire is connected to an amplifier and said amplifier is connected to a recording device.

6. An apparatus according to claim 1 wherein said first and second sensor points are on a line through the center of gravity of the apparatus.

7. An apparatus according to claim 1 wherein said adjusting means extends movably through holes in said first and second plate springs.

8. An apparatus according to claim 1 wherein said second and third sensor points are integral.

9. A method for measuring the shear stiffness characteristic of a structural adhesive comprising a. attaching a pair of apparatuses as defined in claim 5 but of mirror image configuration, one to each glue line edge of a sample comprising two bonded sheets, the first sensor of each apparatus being in contact with one sheet and the second and third sensors of each apparatus being in contact with the other sheet, said apparatuses being attached together through their mounting plate springs, b. applying an external force to said sample, c. recording the movement of said sheets as a result of said force by amplifying the voltage emitted by said transformer and d. transposing said recordings into information indicative the relative strength of said adhesive bond.

* * * * *